US011795717B2

(12) United States Patent
Revilla et al.

(10) Patent No.: US 11,795,717 B2
(45) Date of Patent: Oct. 24, 2023

(54) FLUID CHEMISTRY MANIFOLDS AND SYSTEMS

(71) Applicant: Rheem Manufacturing Company, Atlanta, GA (US)

(72) Inventors: Jorge Miguel Gamboa Revilla, Oxnard, CA (US); Sergio Montalgo Salazar, Oxnard, CA (US); Satya Kiran Gullapalli, Oxnard, CA (US); Kaela Malaki, Oxnard, CA (US)

(73) Assignee: Rheem Manufacturing Company, Atlanta, GA (US)

( * ) Notice: Subject to any disclaimer, the term of this patent is extended or adjusted under 35 U.S.C. 154(b) by 14 days.

(21) Appl. No.: 16/852,823

(22) Filed: Apr. 20, 2020

(65) Prior Publication Data

US 2021/0324649 A1 Oct. 21, 2021

(51) Int. Cl.
*E04H 4/12* (2006.01)
*F16K 27/00* (2006.01)
*C02F 1/00* (2023.01)
*C02F 103/42* (2006.01)

(52) U.S. Cl.
CPC ........... *E04H 4/1209* (2013.01); *C02F 1/008* (2013.01); *F16K 27/003* (2013.01); *C02F 2103/42* (2013.01); *C02F 2209/04* (2013.01); *C02F 2209/06* (2013.01); *C02F 2209/10* (2013.01); *E04H 4/1281* (2013.01)

(58) Field of Classification Search
CPC ..... E04H 4/1209; E04H 4/1281; C02F 1/008; C02F 2209/10; C02F 2209/04; C02F 2209/06; C02F 2103/42; F16K 27/003

USPC ... 210/85, 87, 96.1, 143, 190, 241, 269, 284
See application file for complete search history.

(56) References Cited

U.S. PATENT DOCUMENTS

| | | | | |
|---|---|---|---|---|
| 4,648,043 A | * | 3/1987 | O'Leary | B01F 35/82 700/285 |
| 5,422,014 A | * | 6/1995 | Allen | C02F 1/008 210/139 |
| 5,993,669 A | * | 11/1999 | Fulmer | C02F 1/4674 205/501 |
| 6,003,164 A | * | 12/1999 | Leaders | C02F 1/008 4/493 |

(Continued)

FOREIGN PATENT DOCUMENTS

| KR | 20110002317 A | * | 1/2011 | |
|---|---|---|---|---|
| WO | WO-2019030232 A1 | * | 2/2019 | C02F 1/76 |

*Primary Examiner* — Ekandra S. Miller-Cruz
(74) *Attorney, Agent, or Firm* — Eversheds Sutherland (US) LLP

(57) ABSTRACT

Disclosed herein are fluid chemistry systems comprising fluid chemistry manifolds. The fluid chemistry manifolds can comprise an inlet, two flow paths in fluid communication with the inlet, one or more probe apertures, and an outlet in fluid communication with the two flow paths. The one or more probe apertures can be configured to receive at least a portion of a corresponding fluid chemistry probe. The probe can be configured to detachably attach to the one or more probe apertures and fluidly communicate with the flow path. The probe can include one or more of a pH sensor, an oxidation reduction potential (ORP) sensor, and a total dissolved solids (TDS) sensor. The systems can also comprise an adjustable valve configured to selectively permit a predetermined amount of fluid flow through the at least one of the two flow paths.

13 Claims, 11 Drawing Sheets

(56) References Cited

U.S. PATENT DOCUMENTS

| | | | | |
|---|---|---|---|---|
| 6,026,804 A | * | 2/2000 | Schardt | F28F 27/02 |
| | | | | 165/173 |
| 2008/0264447 A1 | * | 10/2008 | Eyal | C02F 1/4674 |
| | | | | 134/18 |
| 2009/0090665 A1 | * | 4/2009 | Nibler | F28D 1/053 |
| | | | | 210/167.11 |
| 2013/0284649 A1 | * | 10/2013 | Tucker | C02F 1/4674 |
| | | | | 210/139 |
| 2013/0319556 A1 | * | 12/2013 | Prescott | F16L 41/03 |
| | | | | 137/798 |

* cited by examiner

FLUID CHEMISTRY MANIFOLDS AND SYSTEMS

FIELD OF THE DISCLOSURE

The present disclosure relates generally to fluid chemistry manifolds and systems. Particularly, the present disclosure relates to fluid chemistry manifolds and systems for one or more probes.

BACKGROUND

The task of monitoring the properties of water circulation systems is a difficult one that can often require regular professional monitoring. For instance, chlorinated pools often require testing equipment and a trained pool technician to measure the chemistry and quality of water in the pool. Current devices for monitoring water systems are cumbersome and difficult to use. Current systems for monitoring water properties are additionally independent from the systems operating the water circulation systems themselves. Independent monitoring systems can create difficulties for users to maintain and care for their systems. The independent systems may require the user to hire a third-party caretaker, or the independent systems may be electronically inconsistent if the pool manufacturer is different. Generally, existing devices can require frequent replacement of monitoring equipment and/or frequent maintenance on the system due to the exposure of the devices to harsh conditions, such as negative pressure or stagnated water. Improvements in such water monitoring devices for water circulation systems can greatly improve the design space for such technological fields as, for example, irrigation, residential pools, commercial pools, sewage, hydroponics, potable water, water purification, distillation, residential water supply, and the like. Systems and methods to integrate such systems in a user-friendly manner are desirable.

These problems are addressed by the disclosed technology, as well as other needs that will become apparent upon reading the description below in conjunction with the drawings.

SUMMARY

The present disclosure relates generally to fluid chemistry manifolds and systems. Particularly, the present disclosure relates to fluid chemistry manifolds and systems for one or more probes. For example, the disclosed technology can include a fluid chemistry manifold comprising an inlet, two flow paths in fluid communication with the inlet, one or more probe apertures, and an outlet in fluid communication with the two flow paths.

The two flow paths can have a first flow path and a second flow path. The first flow path can have a first diameter, and the second flow path can have a second diameter that is less than the first diameter. The two flow paths can also include a lower flow path positioned at a lower height relative to the ground compared to an upper flow path.

The two flow paths can include an adjustable valve. The adjustable valve can be configured to selectively permit a predetermined amount of fluid flow through at least one of the flow paths. The manifold can also comprise a bypass route from the inlet to the outlet that bypasses the adjustable valve and fluidly communicates with the inlet and the outlet.

Each of the one or more probe apertures can be in fluid communication with one of the flow paths. The probe apertures can also be configured to receive at least a portion of a corresponding fluid chemistry probe. The corresponding probes can be configured to detachably attach to the probe apertures. The probes can include a pH sensor, an oxidation reduction potential (ORP) sensor, and a total dissolved solids (TDS) sensor.

The inlet and the outlet can be in fluid communication with a pool circulation system. In such a manner, the probes can monitor the pool circulation system.

Another example of the present disclosure can include a water heater header cover including an inlet, a flow path in fluid communication with the inlet, and an outlet in fluid communication with the flow path. The water heater header cover can also be in fluid communication with a pool ignition module.

The flow path can comprise one or more probe apertures. Each of the probe apertures can be in fluid communication with one of the flow paths. The probe apertures can also be configured to receive at least a portion of a corresponding fluid chemistry probe. The corresponding probes can be configured to detachably attach to the probe apertures. The probes can include a pH sensor, an oxidation reduction potential (ORP) sensor, and a total dissolved solids (TDS) sensor.

Also disclosed herein are systems and methods utilizing the same.

These and other aspects of the disclosed technology are described herein along with the accompanying figures. Other aspects, features, and elements of the disclosed technology will become apparent to those of ordinary skill in the art upon reviewing the following description of specific examples of the disclosed technology. While features of the disclosed technology may be discussed relative to certain examples and figures, the disclosed technology can include one or more of the features or elements discussed herein. Further, while one or more examples may be discussed as having certain advantageous features, one or more of such features may also be used with the various other examples of the disclosure discussed herein. In similar fashion, while exemplary embodiments may be discussed below as device, system, or methods, it is to be understood that such examples can be implemented in various devices, systems, and methods of the present disclosure.

BRIEF DESCRIPTION OF THE DRAWINGS

The accompanying drawings, which are incorporated in and constitute a part of this specification, illustrate multiple examples of the presently disclosed subject matter and serve to explain the principles of the presently disclosed subject matter. The drawings are not intended to limit the scope of the presently disclosed subject matter in any manner.

DETAILED DESCRIPTION

Figure 1A:
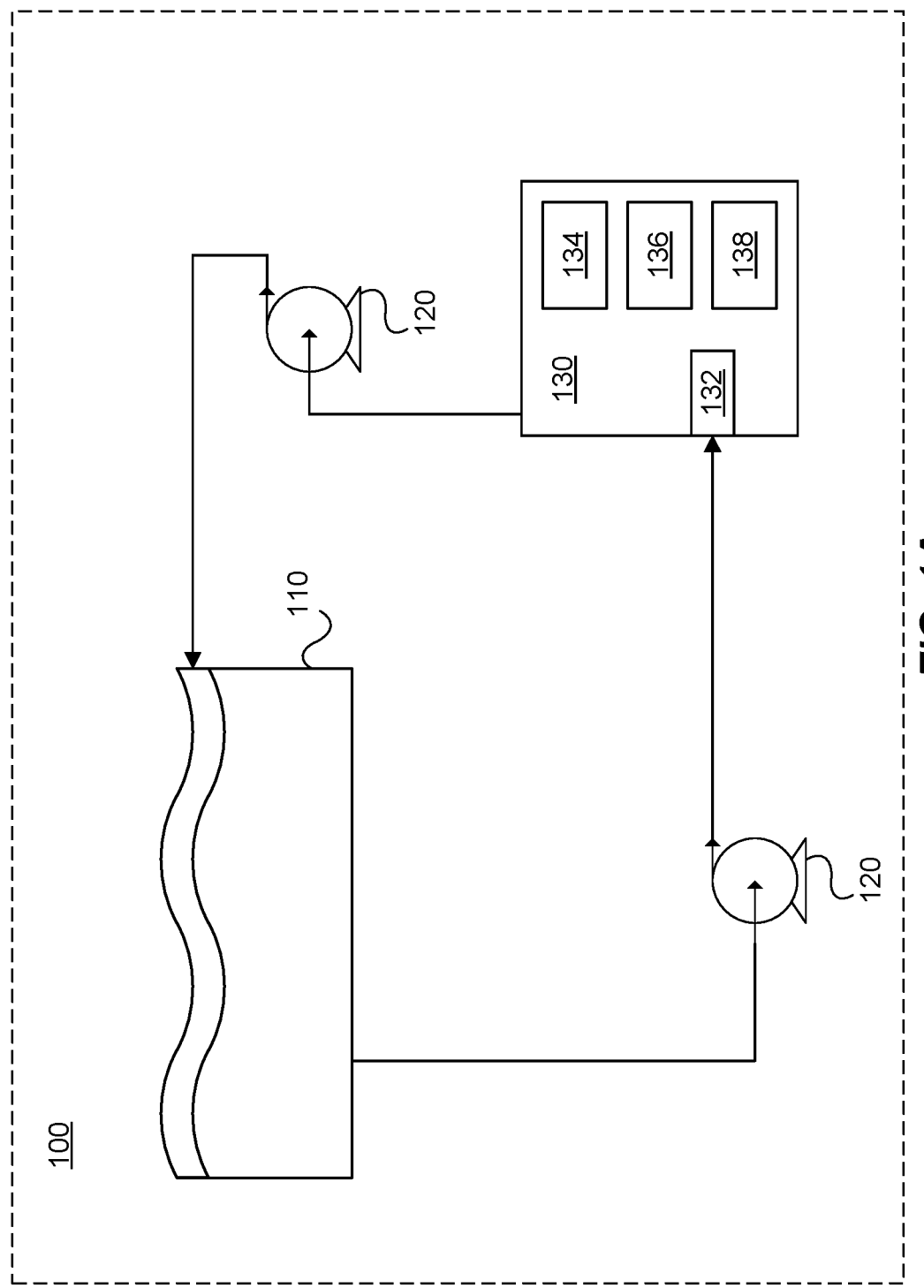
FIG. 1A illustrates an example water circulation system including a water condition controller and a water monitoring device, in accordance with the present disclosure.

Current devices for monitoring water systems are cumbersome and not user-friendly. Such devices often require a trained professional eye and/or third-party monitoring, making them inconvenient for the user. Additionally, the monitoring can create inconsistencies, as the manufacturers of the water systems are not the ones monitoring the system. The manufacturers may be reliant on the users themselves to monitor and maintain their own systems, only being contacted after major damages have occurred. As such, the monitoring systems have no way to correct errors detected in the circulation systems, causing expensive damages and failures.

The present disclosure can provide systems and methods for integrating water condition monitoring with a control system for water circulation systems, such as irrigation, residential pools, commercial pools, sewage, hydroponics, potable water, water purification, distillation, residential water supply, and the like. The present disclosure can provide a water condition monitor and a controller in communication with, for example, a water heater system. The water condition monitor can measure baseline data for one or more water properties. The one or more water properties can include, for example, total dissolved solids (TDS), pH, oxidation reduction potential (ORP), temperature, flow rate, and the like. The controller can also perform a calibration based on baseline data to determine a normal operating range for each of the water properties. The water condition monitor can continually receive operation water data from the system during normal operation. The operational data can then be compared to the normal operating range to ensure the values of the water properties are normal. If a value for one of the water properties is outside the normal operating range, the value can be designated as an anomaly. The controller can then determine one or more predetermined corrective actions and output instructions to the system to perform the one or more predetermined corrective actions to correct the anomaly.

Although certain examples of the disclosure are explained in detail, it is to be understood that other examples or applications of the disclosed technology are contemplated. Accordingly, it is not intended that the disclosure is limited in its scope to the details of construction and arrangement of components set forth in the following description or illustrated in the drawings. Other examples or applications of the disclosure are capable of being practiced or carried out in various ways. Also, in describing the examples, specific terminology will be resorted to for the sake of clarity. It is intended that each term contemplates its broadest meaning as understood by those skilled in the art and includes all technical equivalents which operate in a similar manner to accomplish a similar purpose.

Herein, the use of terms such as "having," "has," "including," or "includes" are open-ended and are intended to have the same meaning as terms such as "comprising" or "comprises" and not preclude the presence of other structure, material, or acts. Similarly, though the use of terms such as "can" or "may" are intended to be open-ended and to reflect that structure, material, or acts are not necessary, the failure to use such terms is not intended to reflect that structure, material, or acts are essential. To the extent that structure, material, or acts are presently considered to be essential, they are identified as such.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified.

The components described hereinafter as making up various elements of the disclosure are intended to be illustrative and not restrictive. Many suitable components that would perform the same or similar functions as the components described herein are intended to be embraced within the scope of the disclosure. Such other components not described herein can include, but are not limited to, for example, similar components that are developed after development of the presently disclosed subject matter.

As used herein, the terms "steady-state" or "near-steady-state" are meant to describe a system or process wherein the variables (i.e., properties) defining the behavior of the system or process are unchanging with respect to time. That is to say, in continuous time, the partial derivate of any given variable at "steady-state" or "near-steady-state" with respect to time is at or near zero.

Reference will now be made in detail to examples of the disclosed technology, such as those illustrated in the accompanying drawings. Wherever convenient, the same references numbers will be used throughout the drawings to refer to the same or like parts.

FIG. 1A illustrates a water circulation system in accordance with the present disclosure. By way of illustration, and not limitation, FIG. 1 is illustrated as a water heater system 100 for a pool 110. The water heater system 100 can comprise one or more pumps 120 and a heater 130. The heater 130 can include an intake manifold 132, an ignition module 134, a water condition monitor 136, a controller 138, and/or other components useful for heating a fluid, such as water. It is to be understood that the water condition monitor 136 and the controller 138 need not be components of a heater 130, and can instead be located in other parts of the water heater system 100. For instance, the water condition monitor 136 can be a separate and distinct device located in the pool 110 and can communicate with the controller 138. Other configurations are contemplated. The water heater system 100 can be configured to circulate water via the pumps 120. The water heater system 100 can include other components such as valves, heat exchangers, diverters, coolers, and the like.

The water condition monitor 136 can be located in or as part of the header of the water heater system 100. For illustration, an example header cover for the water heater system 100, which includes a water condition monitor 136, is discussed in greater detail below with respect to FIGS. 7A and 7B. The water condition monitor 136 can be located in the intake manifold 132. An example of the intake manifold 132 including a water condition monitor 136 is discussed in greater detail below with respect to FIG. 5. The intake manifold 132 can be in direct fluid communication with one or more components of the water heater system (e.g., a pump 120, a pipe, tubing, or other component(s)). Thus, the intake manifold 132 can be configured to ensure the water condition monitor 136 is in communication with water (or other fluid) of the water heater system 100. The water condition monitor 136 is illustrated by the probes 610 in FIGS. 6A and 6B. Regardless of whether the water condition monitor 136 is integrated into the header, the water condition monitor 136 can be constructed or positioned such that water continuously flows through or across the water condition monitor during normal operating conditions of the water heater system. The intake manifold 132 can also be configured to constantly produce a constant or near-constant flow of water across the water condition monitor 136, which can help prevent the water condition monitor 136 from measuring stagnant water and can encourage the water condition monitor 136 to measure water properties at a near-steady-state condition. For instance, the intake manifold 132 can ensure a pressure drop is present that would ensure at least partial flow through the intake manifold 132. As will be appreciated, measuring the water properties at steady-state or near-steady-state conditions ensures that any deviations from normal behavior are distinguishable (i.e., measuring the water properties at steady-state or near-steady-state conditions minimizes or eliminates "noise" in the measurements that could arise from local concentrations of contaminants, for example).

The water condition monitor 136 can be configured to monitor one or more water properties. For instance, the water condition monitor 136 can include a temperature sensor, a pH sensor, an oxidation reduction potential (ORP) sensor, a total dissolved solids (TDS) sensor, a chlorine concentration sensor, and/or a flow rate sensor. Other sensors can be used to obtain additional properties of the one or more water properties. The various sensors of the water condition monitor 136 can gather operational water data for one or more water properties, and the water condition monitor 136 can transmit the water data to other components. The water condition monitor 136 can include a communication module that can communicate with one or more components of the water heater system 100 (e.g., the controller 138). The communication module of the water condition monitor 136 can be configured to communicate wirelessly using any useful method or technology or via wired communication. As an example, the water condition monitor 136 can be configured to communicate via the communication module with the ignition module 134 of the heater 130. As additional examples, the water condition monitor 136 can be configured to electrically communicate with other components of the water heater system 100, such as burners, pumps 120, heat pumps, hydronic units, valves, and the like.

Figure 1B:
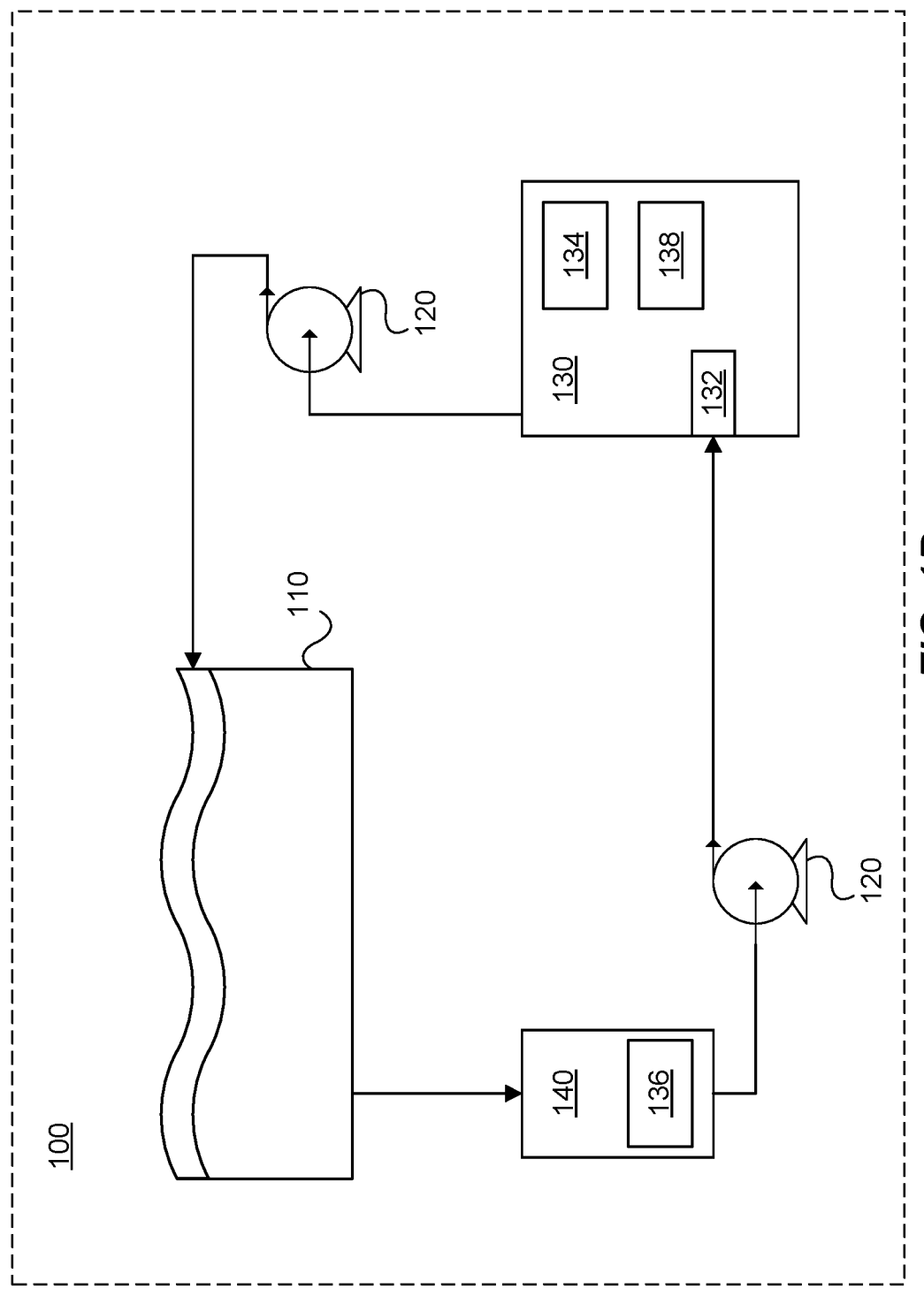
FIG. 1B illustrates an example water circulation system including a water condition controller and a water monitoring device, in accordance with the present disclosure.

Alternatively, the water condition monitor 136 can included in a separate and distinct water condition monitor apparatus 140 that can include a fluid inlet and a fluid outlet, and the water condition monitor apparatus 140 can be configured to connect to the fluid circuit of the water heater system 100 (e.g., to a pump 120, a pipe, a tube, or some other component of the water heater system 100 that permits the water condition monitor 136 to be in fluid communication with water or other fluid of the water heater system 100) via the fluid inlet and/or fluid outlet. As shown in FIG. 1B, the water condition monitor 136 can be located within the water condition monitor apparatus 140 such that the water condition monitor 136 is in communication with fluid passing through the water condition monitor apparatus 140 when it is connected to the fluid circuit of the water heater system 100. The water condition monitor apparatus 140 can itself include a manifold, which can be disposed between the fluid inlet and fluid outlet of the water condition monitor 136. The water condition monitor 136 can be located within the manifold of the water condition monitor apparatus 140. Examples of the manifold 132 and water condition monitor apparatus 140 are discussed in greater detail below with reference to FIGS. 5-7.

The water condition monitor apparatus 140 can provide modular connection to the water heater system 100 such that a user can easily attach and/or detach the water condition monitor apparatus 140 to any water heater system 100 or any position in the water heater system 100. The water condition monitor apparatus 140 can include a communication module that can communicate with one or more components of the water heater system 100 (e.g., the controller 138). The communication module of the water condition monitor apparatus 140 can be configured to communicate wirelessly using any useful method or technology or via wired communication. As an example, the water condition monitor apparatus 140 can be configured to communicate via the communication module with the ignition module 134 of the heater 130. As additional examples, the water condition monitor apparatus 140 can be configured to electrically communicate with other components of the water heater system 100, such as burners, pumps 120, heat pumps, hydronic units, valves, and the like.

Figure 2:
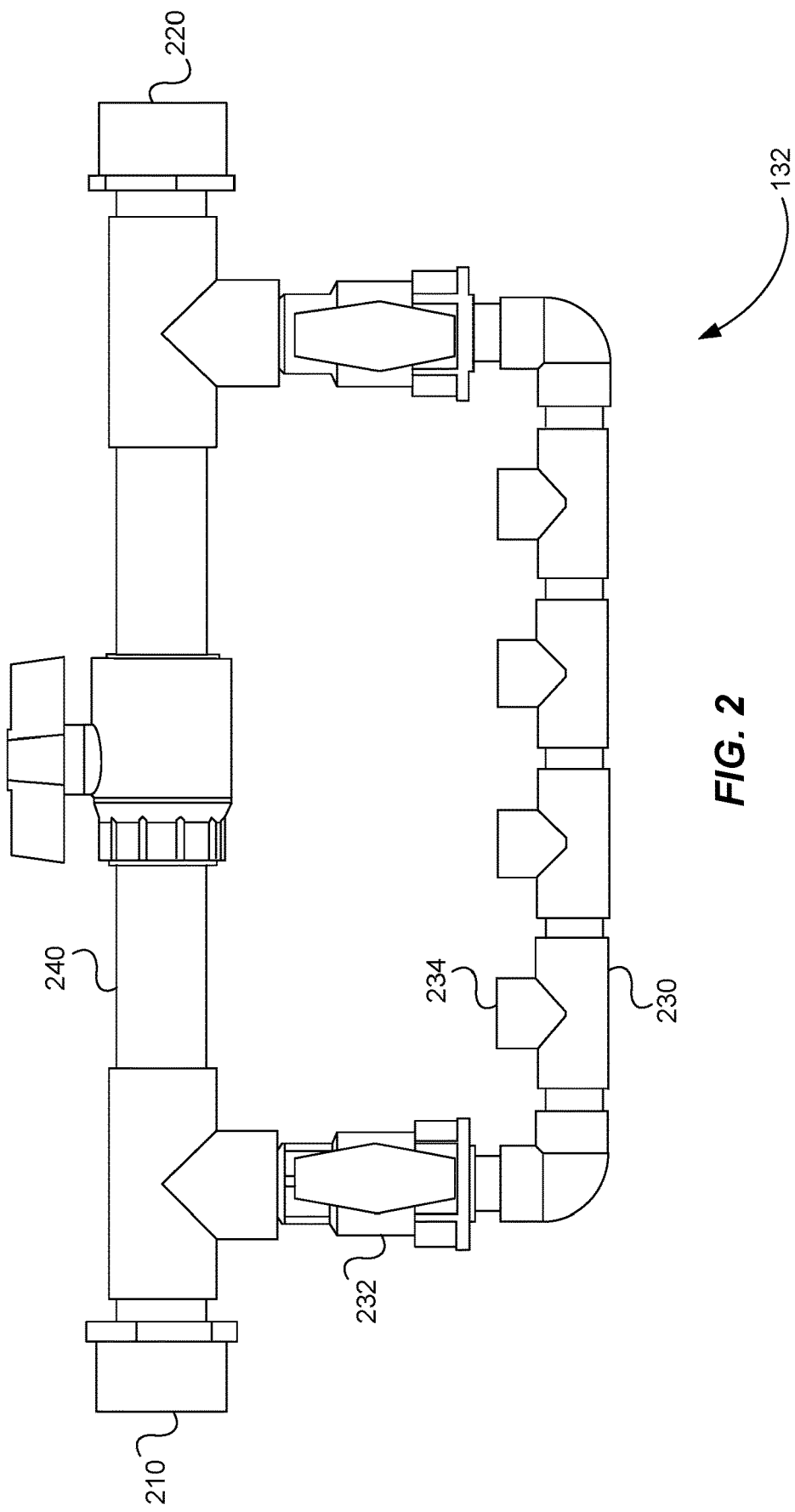
FIG. 2 illustrates a side view of an example water condition monitor apparatus, in accordance with the present disclosure.

Referring now to FIG. 2, an example fluid chemistry manifold 132 is illustrated. As mentioned above, the fluid chemistry manifold 132 can be integral with the water condition monitor apparatus 140. As shown, the fluid chemistry manifold 132 can comprise an inlet 210, an outlet 220, and two or more flow paths in fluid communication with the inlet 210 and the outlet 220, including a first flow path 230 and a second flow path 240. One or more of the flow paths flow paths (e.g., the first flow path 230, as illustrated) can include an adjustable valve 232. Additional adjustable valves can be present. The manifold 132 can include one or more probe apertures 234, and each probe aperture 234 can be configured to receive a probe for monitoring and/or measuring various aspects and attributes related to the fluid chemistry of fluid passing through the manifold 132. As shown, the manifold 132 can include four probe apertures 234, although any number of probe apertures 234 is contemplated. For example, the manifold 132 can include one, two, three, five, six, or any other number of probe apertures 234. The probe apertures 234 can be disposed along one or more flow paths of the manifold 132. As illustrated in FIG. 2, the probe apertures can be located along the first fluid flow path.

The probe apertures 234 can include a mechanism for securely retaining installed fluid chemistry probes. For example, the probe apertures 234 can include screw threading on an interior surface of the probe apertures 234 configured to receive corresponding screw threading on one or more probes. The probe apertures 234 can be configured to detachably receive one or more probes in a variety of other ways, such as any combination of interference fits, friction fits, threaded fits, locking nuts, glue, epoxy, other adhesives, and the like. The probe apertures 234 can also include fasteners and/or attachment elements (e.g., any combination of screws, latches, pins, locks, snaps, clips, and the like) configured to fasten the one or more probes to the probe apertures 234.

The inlet 210 and the outlet 220 can be configured to attach to the water heater system 100. For instance, the inlet 210 and the outlet 220 can detachably attach to piping used to circulate water through the water heater system 100. The inlet 210 and the outlet 220 can detachably attach to the water heater system 100 through a variety of means, such as any combination of screw threading, interference fit, friction fit, locking nuts, glue, epoxy, other adhesives, gaskets, and the like. The inlet 210 and the outlet 220 can also include fasteners and/or attachment elements, such as latches, pins, locks, snaps, clips, and the like, configured to fasten the inlet 210 and the outlet 220 to the water heater system 100.

The various flow paths can have substantially similar diameters. Alternatively, at least some of the flow paths can have different diameters. For instance, one flow path, such as the first flow path 230, can have a first diameter, and another flow path, such as the second flow path 240, can have a second diameter that is different from the first diameter. The first flow path 230 and the second flow path 240 can have a predetermined ratio of diameters, which can result in a differential of fluid flow between the two flow paths 230, 240. In other words, the first flow path 230 can have a first flow percentage (i.e., a percentage of the total flow of the manifold 132 when all valves are open and fluid is permitted to flow freely through either flow path 230, 240), and the second flow path 240 can have a second flow percentage. The first flow path 230, as shown, can have a first diameter less than the second diameter or vice-versa. One of the flow paths can be positioned or located at a lower height as compare to the height of at least one other flow path. For instance, the first flow path 230 can be positioned at a lower height relative to the ground than the second flow path 240.

Figure 3A:
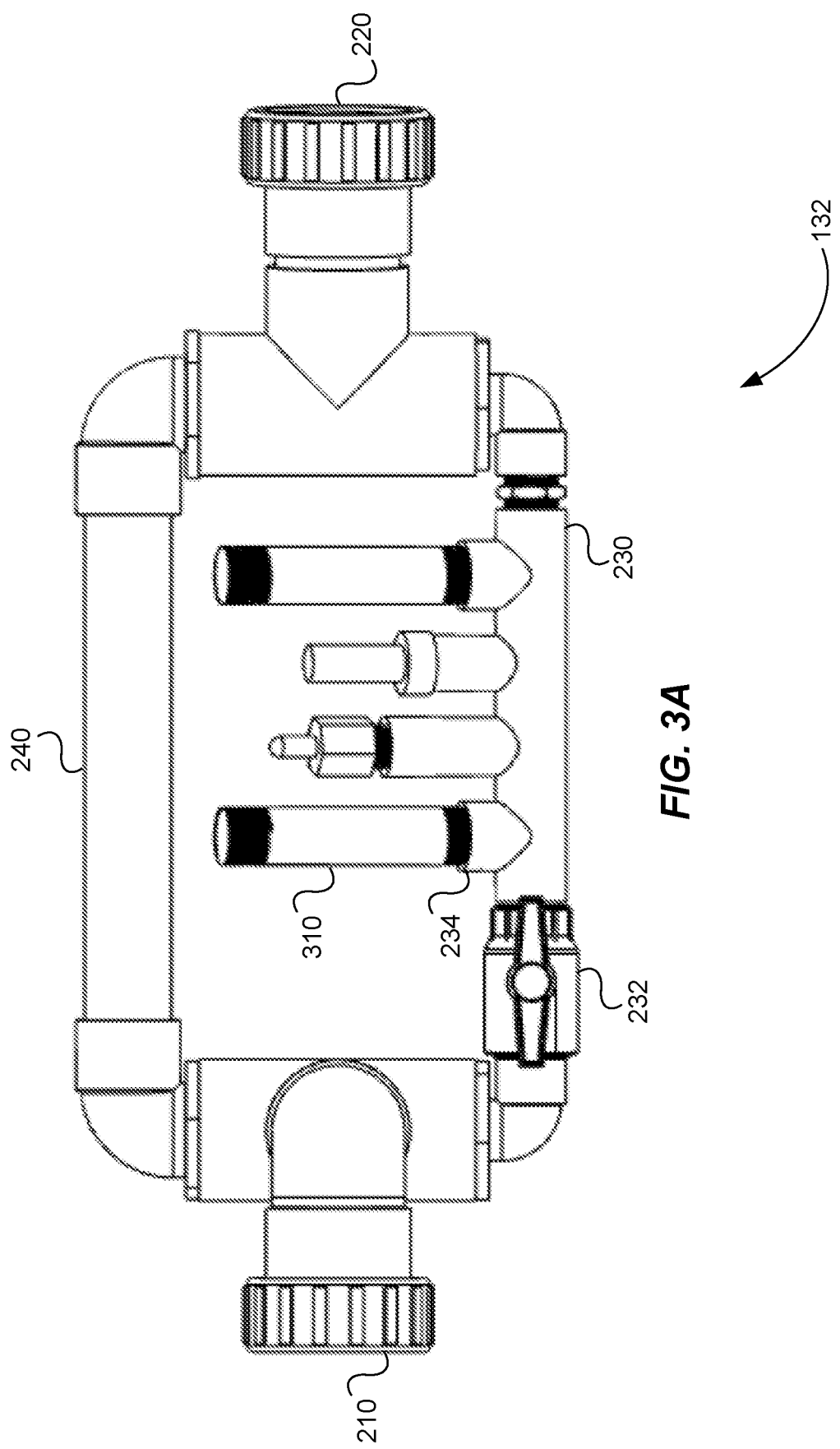
FIG. 3A illustrates a side view of another example water condition monitor apparatus, in accordance with the present disclosure.
Figure 3B:
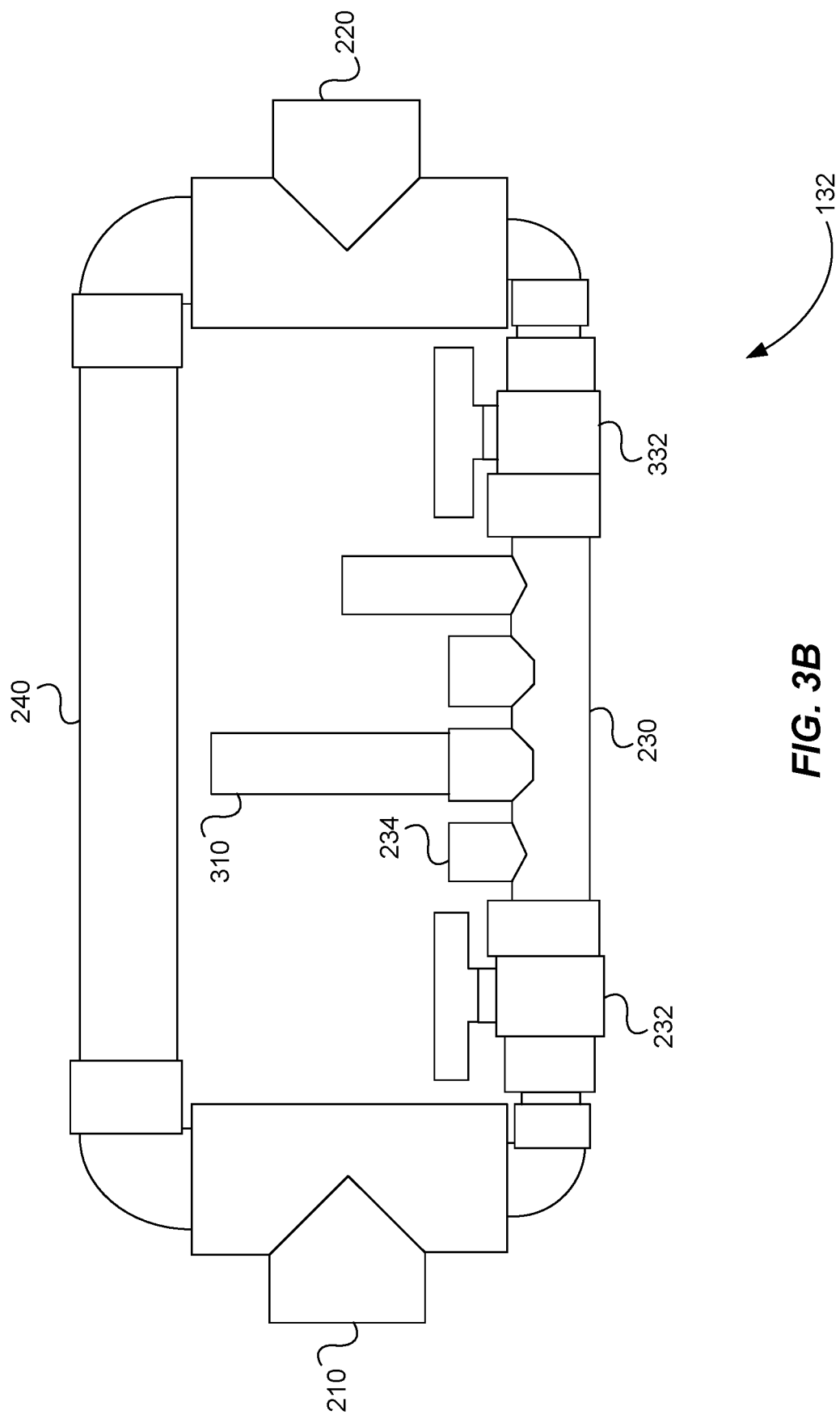
FIG. 3B illustrates a side view of another example water condition monitor apparatus, in accordance with the present disclosure.

As shown in FIG. 3A and FIG. 3B, the one or more probe apertures 234 can be configured to receive a portion of a corresponding one or more fluid chemistry probes 310. As explained above, the probes 310 can detachably insert and/or attach to a corresponding probe aperture 234 via a variety of manners, mechanisms, and/or substances. The probes 310 can include a pH sensor 552, a total dissolved solids (TDS) sensor 554, an oxidation reduction potential (ORP) sensor 555, a flow rate sensor 556, and a concentration sensor (e.g., air concentration, chlorine concentration, lead concentration) 558. Other probes can be present, such as viscosity sensors, density sensors, temperature sensors, pressure transducers, and any sensors known to measure a desirable property of the water heater system 100. Optionally, a single probe 310 can include a variety of sensors, such as the sensors expressly mentioned here and/or other sensors, and/or the single probe 310 can be otherwise configured to detect and measure multiple characteristics or attributes.

Also illustrated by FIG. 3A and FIG. 3B are the various configurations of the two flow paths and the adjustable valve 232. As shown in FIG. 3A, the adjustable valve 232 can be positioned on and/or in fluid communication with the first flow path 230. The first flow path 230 can be positioned below the second flow path 240, and the first flow path 230 can have a first diameter less than the second diameter of the second flow path 240. As shown in FIG. 3B, the fluid chemistry manifold 132 can include a check valve 332. The check valve 332 can ensure unidirectional flow and can also prevent backflow. The check valve 332 can also work in conjunction with the adjustable valve 232 to seal off the aperture(s) 234. In such a manner, one or more probes 310 can be easily inserted, removed, swapped out, and/or undergo maintenance without requiring an invasive shutdown of the system 100 outside of the fluid chemistry manifold 132.

Figure 4A:
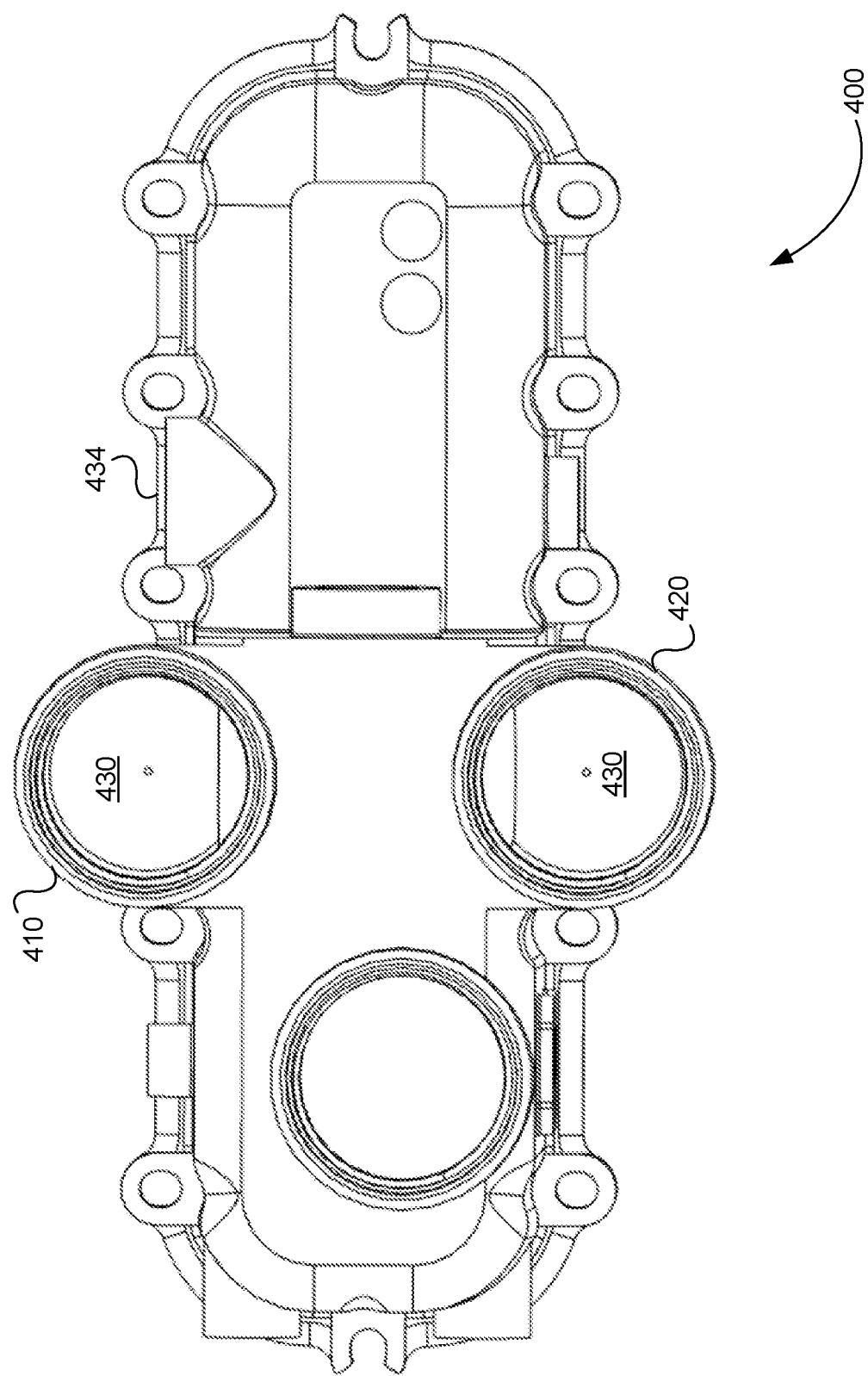
FIG. 4A illustrates a side view of an example water heater header cover, in accordance with the present disclosure.
Figure 4B:
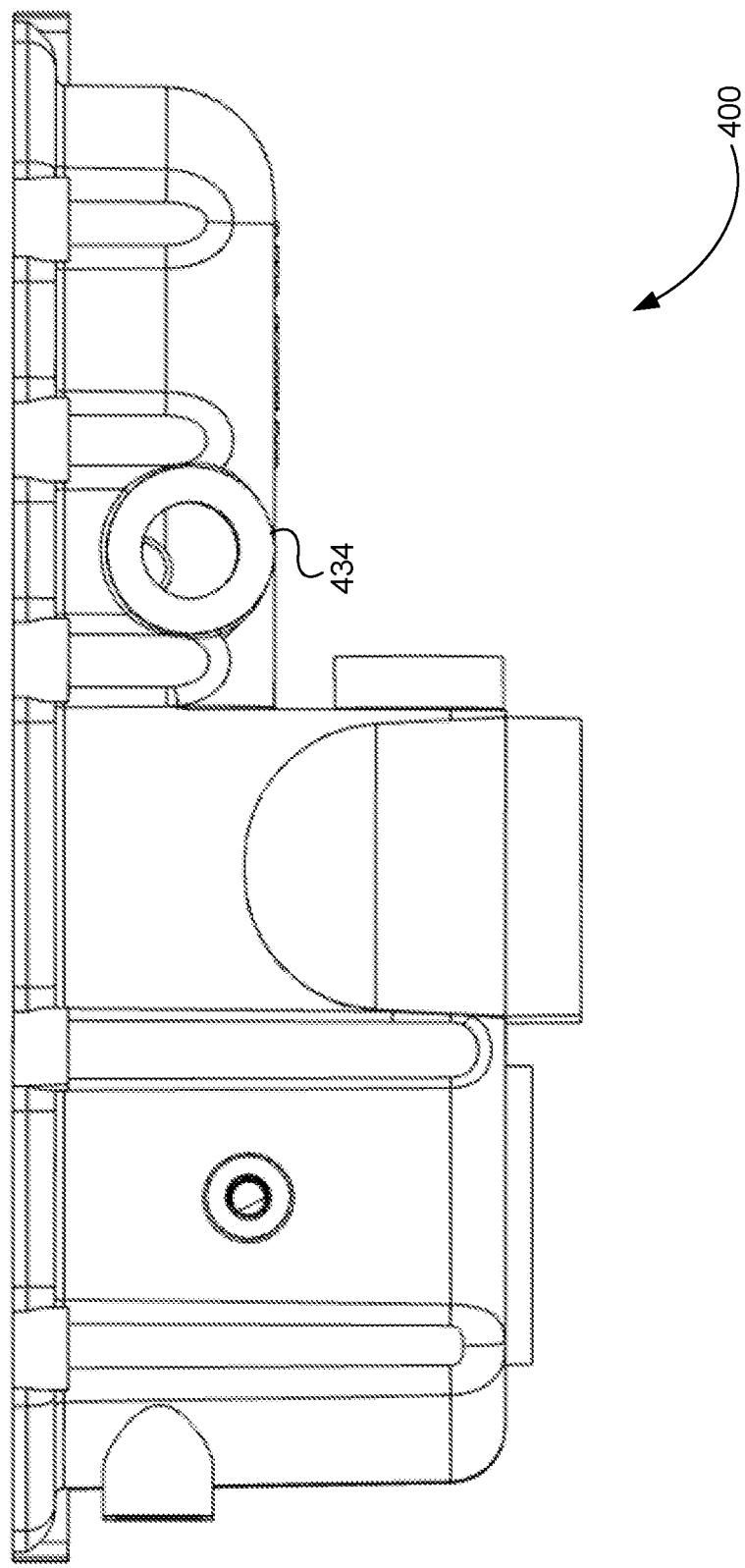
FIG. 4B illustrates a top view of an example water heater header cover, in accordance with the present disclosure.

FIG. 4A and FIG. 4B illustrate an example water heater header cover 400. The disclosed water heater header cover 400 can be a component of the water condition monitor apparatus 140. The water heater header cover 132 can alternatively, or additionally, be in communication with one or more components of the heater 130, such as the ignition module 134 and the like. The water heater header cover 400 can include an inlet 410, an outlet 420, and a flow path 430 in communication with the inlet 410 and the outlet 420. The flow path 430 can include one or more probe apertures 434 configured to receive at least a portion of a corresponding fluid chemistry probe. Optionally, the water heater header cover 400 can comprise a bypass route (not shown) to transport fluid between the inlet 410 and the outlet 420 without entering the header cover. In such an example, the one or more probe apertures 434 can be in fluid communication with the bypass route. The bypass route can have a similar configuration to the examples discussed above with respect to FIGS. 2, 3A, and 3B. In addition or alternatively, the water heater header cover 400 can include a bypass route that is not directly attached or connected to the water heater header cover's main inlet 410 and outlet 420. For example, the water heater header cover 400 can include a separate bypass outlet (not shown) and a separate bypass return inlet (not shown), each of which can be configured to receive or otherwise connect to an end of a bypass conduit or pipe (not shown). The bypass pipe can include one or more probe apertures 434 such that one or more probes can be placed in fluid communication with fluid flowing into the water heater header cover 400 and into the bypass pipe via the bypass outlet, ultimately returning to the water heater header cover 400 via the bypass return inlet. Regardless of the type of bypass used, a bypass route can be advantageous in water heater header cover 400 designs as such designs are often in close proximity to neighboring or adjacent components, and in at least some scenarios, it may be difficult to incorporate a probe into the water heater header cover but for a bypass route.

In the water heater header cover 400, the one or more probe apertures can be configured to receive at least a portion of one probe. The one probe can be configured to measure multiple properties at once. The probe can also be in electrical communication with the pool ignition module 134 to send and/or receive data. In such a manner, the water heater header cover 400 can be fluidly and electrically integrated into the water heater system 100. The probe can include a pH sensor 552, a total dissolved solids (TDS) sensor 554, an oxidation reduction potential (ORP) sensor 555, a flow rate sensor 556, and a concentration sensor (e.g., air concentration, chlorine concentration, lead concentration) 558. Other probes can be present, such as viscosity sensors, density sensors, temperature sensors, pressure transducers, and any sensors known to measure a desirable property of the water heater system 100.

The probe apertures 434 can include a mechanism for securely retaining installed fluid chemistry probes. For example, the probe apertures 434 can include screw threading on an interior surface of the probe apertures 434 configured to receive corresponding screw threading on one or more probes. The probe apertures 434 can be configured to detachably receive one or more probes in a variety of other ways, such as any combination of interference fits, friction fits, threaded fits, locking nuts, glue, epoxy, other adhesives, and the like. The probe apertures 434 can also include fasteners and/or attachment elements (e.g., any combination of screws, latches, pins, locks, snaps, clips, and the like) configured to fasten the one or more probes to the probe apertures 434.

The inlet 410 and the outlet 420 can be configured to attach to the water heater system 100. For instance, the inlet 410 and the outlet 420 can detachably attach to piping used to circulate water through the water heater system 100. The inlet 410 and the outlet 420 can detachably attach to the water heater system 100 through a variety of means, such as any combination of screw threading, interference fit, friction fit, locking nuts, glue, epoxy, other adhesives, gaskets, and the like. The inlet 410 and the outlet 420 can also include fasteners and/or attachment elements, such as latches, pins, locks, snaps, clips, and the like, configured to fasten the inlet 410 and the outlet 420 to the water heater system 100.

Figure 5:
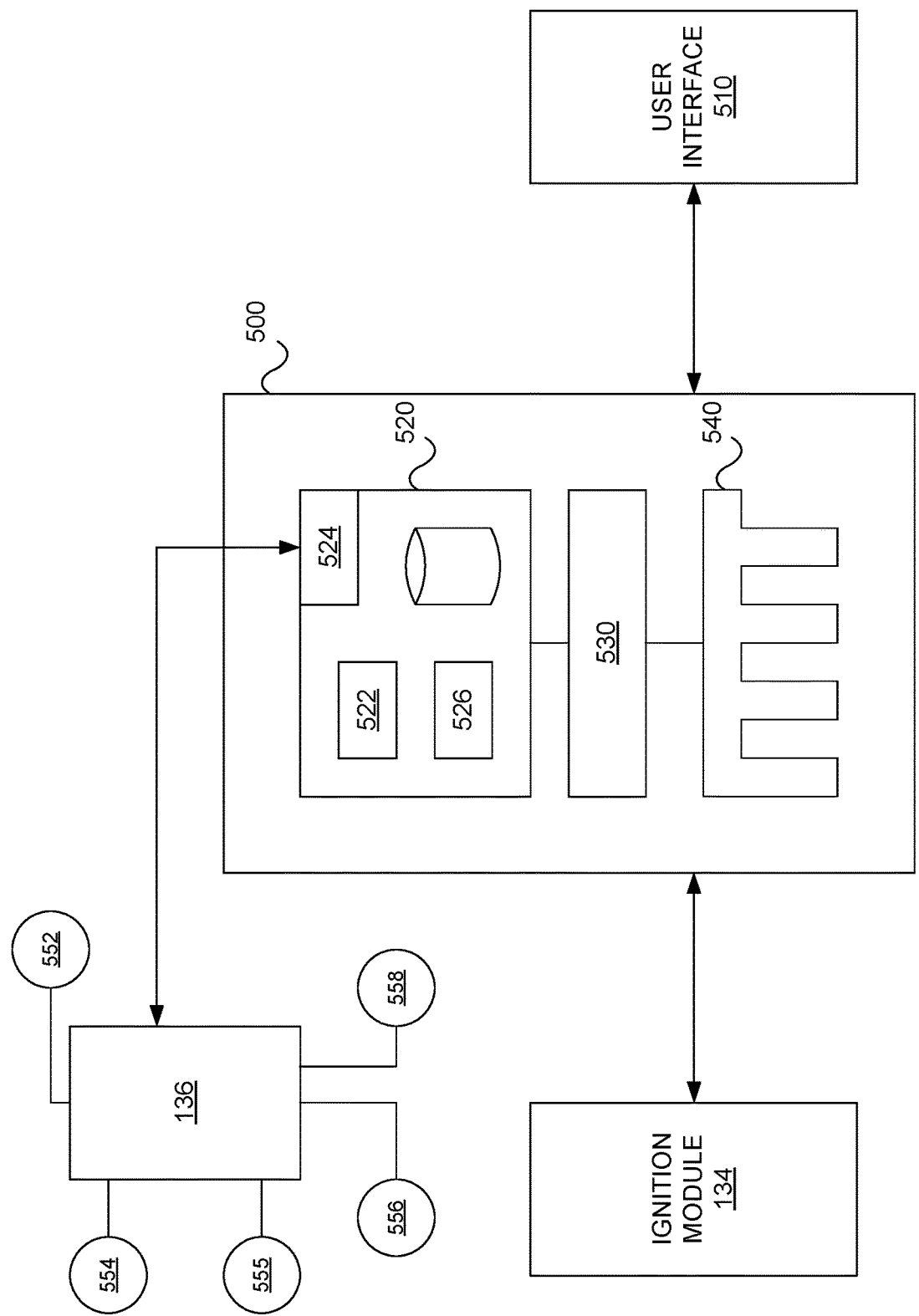
FIG. 5 illustrates an example water condition controller and water monitoring device, in accordance with the present disclosure.

As shown in FIG. 5, the water condition monitor 136 (and/or the water condition monitor apparatus 140) can be in communication with a water condition controller 500 in accordance with the present disclosure. The water condition controller 500 can be in wired and/or wireless communication with the water condition monitor 136, the water condition monitor apparatus 140, and/or various components of the water heater system 100, such as the ignition module 134, the heater 130, or other system components such as pumps 120, valves, and the like. The water condition controller 500 can also be in communication with a user interface 510. The user interface 510 can be configured to transmit and receive information from the water condition controller 500. Some or all of the user interface 510 can be integrated with the water condition controller 500, such as a keypad and/or touchscreen, or some or all of the user interface 510 can be separate but in electrical communication with the water condition controller 500. For example, the user interface 510 can be provided by a program or application on a mobile, a tablet, a personal computer, and the like.

As shown, the water condition controller 500 can comprise a command module 520, a controller 530, and a connector 540. The command module 520 can comprise one or more processors 522, a transceiver 524 in communication with the water condition monitor 136 and processors 522, and a memory 526 in communication with the one or more processors 522. The components described herein can further be in electrical communication with each other, as well as with other components of the water condition controller 500. The memory 526 can store various instructions, programs, databases, machine learning algorithms, models, and the like, such as an operating system (OS). The memory 526 can communicate with the processors 522 to, for instance, execute programs, store data, communicate with other components, and the like. The processors 522 can also facilitate external communication via the other components of the water condition controller 200. For example, the processors 522 can communicate via the transceiver 524 over a network with various systems, such as a security system or a data logging system. The processors 522, via the transceiver 524, can also be in communication with one or more storage devices for storing datasets, documents, instructions, programs, and the like.

The controller 530 can be in communication with the command module 520 via the various components of the command module 520. Alternatively, the controller 530 and the command module 520 can be embodied in the same component. For example, the controller 530 and the command module 520 can be separate processors or one singular processor. The controller 530 can be any analog or non-analog controller. For instance, the controller 530 can comprise one or more switches configured to affect desired changes to the water heater system 100. In such a manner, the command module 520 can output one or more corrective actions to be implemented on the water heater system 100 by the controller 530.

The transceiver 524 can receive data from the water condition monitor 136. In such a manner, a pipeline of data can be constructed by receiving data from the water condition monitor 136, processing the data at the controller 530, and outputting one or more corrective actions, if necessary. As shown, the water condition monitor 136 can comprise a pH sensor 552, a total dissolved solids (TDS) sensor 554, an oxidation reduction potential (ORP) sensor 555, a flow rate sensor 556, a concentration sensor (e.g., air concentration, chlorine concentration, lead concentration) 558. Other sensors can be present on the water condition monitor 136, such as viscosity sensors, density sensors, temperature sensors, pressure transducers, and any sensors known to measure a desirable property of the water heater system 100. Each of the sensors can collect data relating to one or more water properties of the water heater system 100 and relay the data from the water condition monitor 136 to the command module 520 via the transceiver 524.

The controller 130 can associate detected anomalies in the water data with one or more corrective actions. For example, if the normal operating range for temperature is not to exceed 100° F., and the temperature sensor on the water condition monitor 136 reads 112° F., the controller 230 can shut down one or more water boilers. As another example, if the TDS data exceeds a predetermined safe operating range, the controller 130 can instruct the one or more pumps 120 to decrease operating speed or even shut down to prevent damage to components of the pumps, such as impellers. The one or more corrective actions can be based on historical data, such as maintenance that has previously remedied a same or similar anomaly. Corrective actions can include such actions as: emergency shut down of the water heater system 100, altering a flow rate (e.g., adjusting performance of one or more pumps), altering a temperature (e.g., adjusting performance of a burner), and the like.

By way of another example, the pH sensor 552 can detect that the pH value of the water data is low and designate the pH data as an anomaly. Low pH values can cause a corrosive environment to form, damaging filtration components, pipes, and the like. In response, the controller 130 can instruct the water heater system 100 (via one or more components) or the user (via the user interface 510) to add chlorine to the water heater system 100 to increase the alkalinity of the system. Although example relates expressly to pH levels, the disclosed technology can provide similar benefits and functionalities in relation to other aspects of the system's water chemistry.

As another example, the controller 130 can be configured to maintain a historical record of water chemistry for a given water heater system 100 or a given type of water heater system 100, which can influence changes to suggested maintenance schedules, future design changes, and the like. A historical record of water chemistry can also provide documentation for warranty disputes or other issues.

Figure 6A:
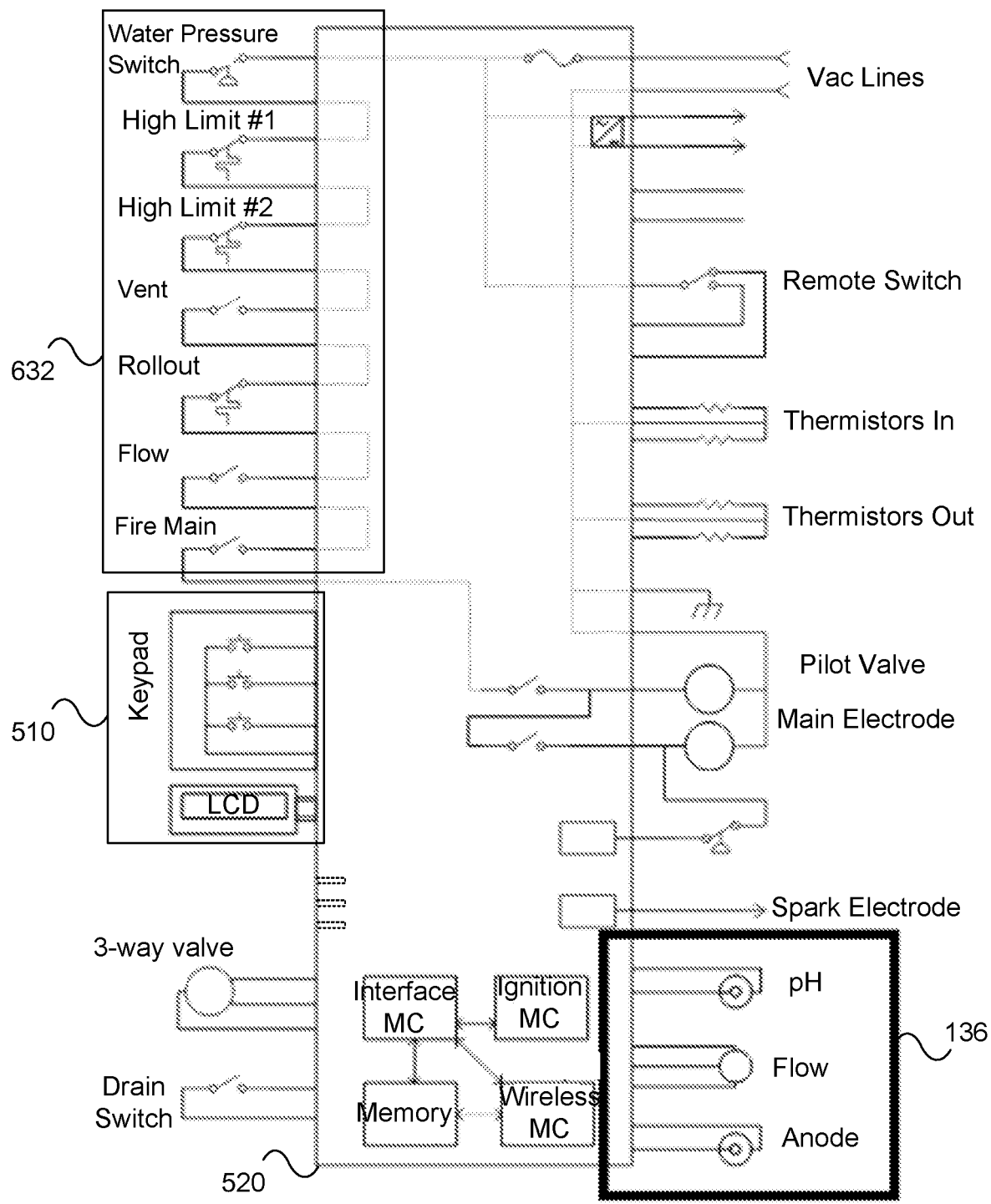
FIG. 6A illustrates an example water condition controller and an example water monitoring device, in accordance with the present disclosure.
Figure 6B:
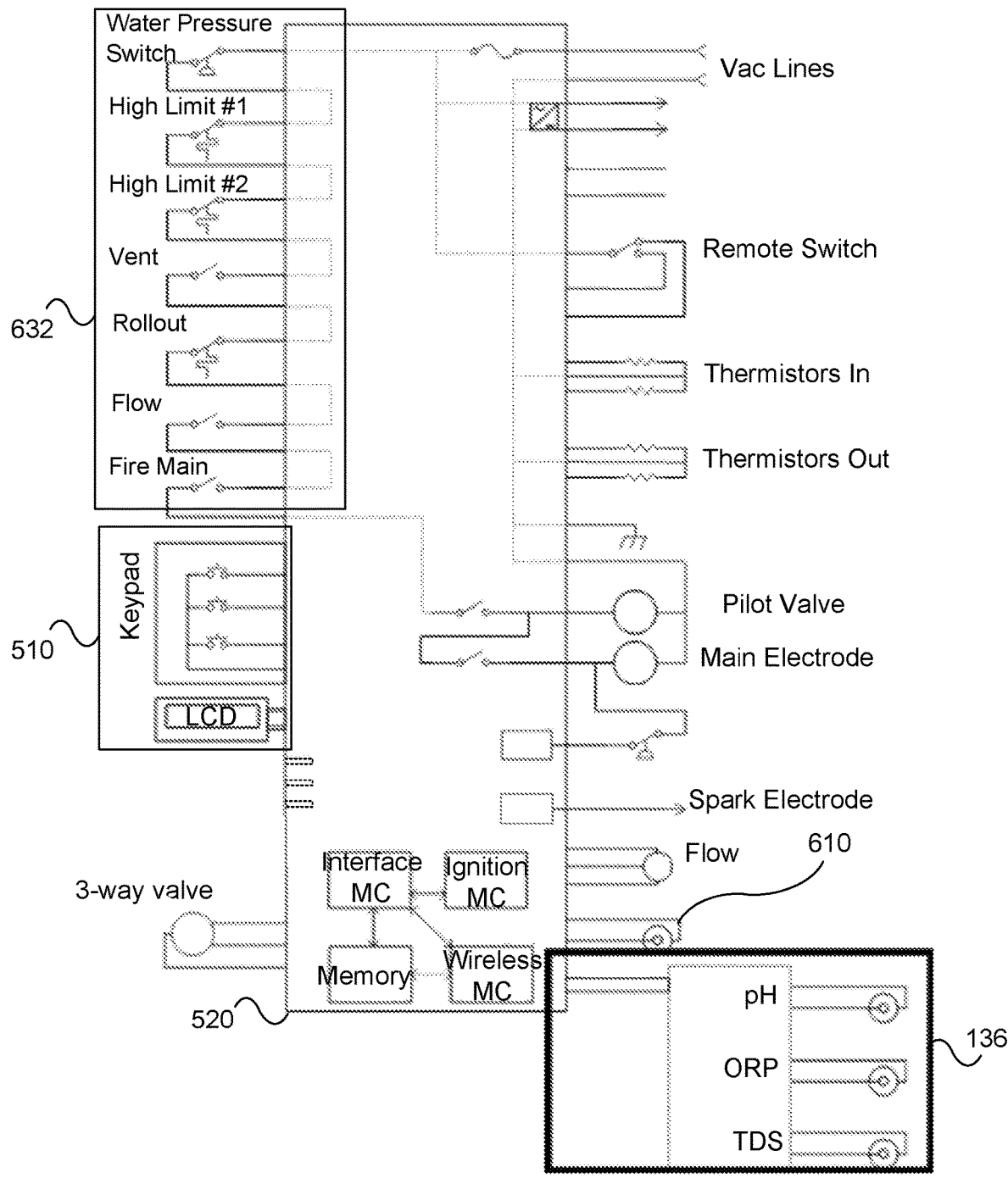
FIG. 6B illustrates an example water condition controller and an example water monitoring device, in accordance with the present disclosure.

FIGS. 6A and 6B illustrate system diagrams of a water condition controller 500. As shown in FIG. 6A, the water condition monitor 136 can be directly connected to (or include) the command module 220520 Whereas alternatively, the water condition monitor 136 can be separate and distinct while still in communication with the command module 520, as shown in FIG. 6B. The command module 520 can further be in communication with a sacrificial anode 610 to prevent or reduce corrosion of components in the water heater system 100, and the controller 530 comprising one or more switches 632.

As shown, the user interface 510 can comprise a keypad for user input, as well as a screen to provide information to the user. The user interface 510 can be directly in communication with the command module 520, as shown, but it is understood that the user interface 510 can be provided separately in communication with the command module, such as on a mobile device. For example, the user interface 510 can be provided as an application on a mobile device. The application can also be configured to transmit interactions to the command module 520.

The example water condition controller 500 shown in FIGS. 6A and 6B are shown and described relating to a heated pool circulation system as the water heater system 100. However, it is understood that the water condition controllers of the present disclosure can be used in a variety of applications. Other components of the water condition controller 500 can be included or excluded depending on the desired application of the water condition controller 500.

While the following methods are described with reference to the water condition controller 500, it is understood that one or more method steps or whole methods can be performed by other systems, general-purpose computers, computer operators, and the like.

Figure 7:
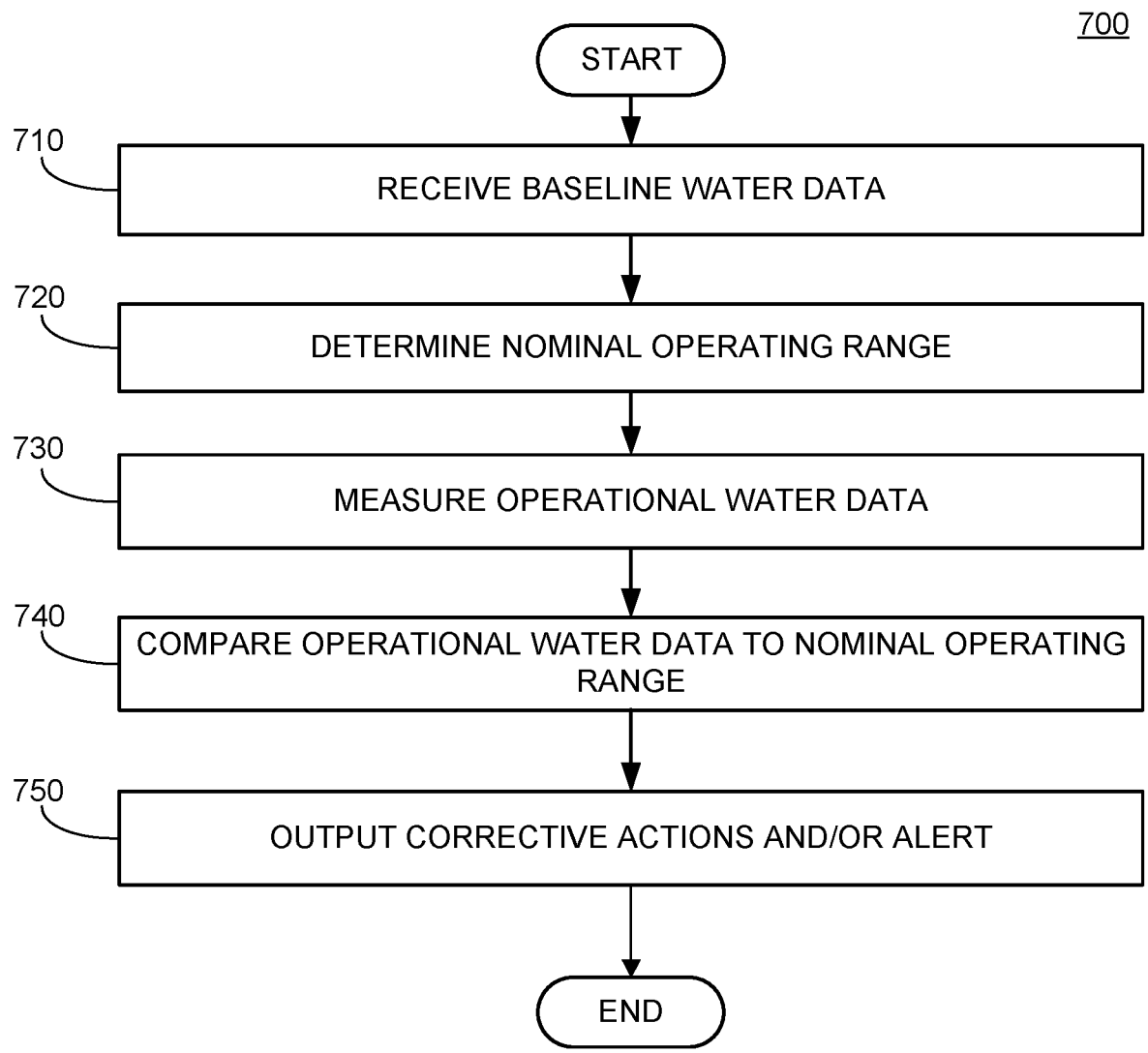
FIG. 7 illustrates a flowchart of an example method for monitoring the condition of water, in accordance with the present disclosure.

FIG. 7 illustrates a method 700 for monitoring the condition of water in accordance with the present disclosure. As shown in block 710, the water condition monitor 136 can receive baseline water data. The baseline water data can be indicative of one or more water properties measured by the water condition monitor 136. The one or more water properties (e.g., as discussed above) can include, but are not limited to, pH, TDS, ORP, flow rate, concentration, and temperature. The water condition monitor 136 can transmit the measured data for the one or more water properties to the command module 520 a (e.g., to the transceiver 524 of the command module 520). The command module 520 can receive the measured data and can then process, store, and/or transmit the measured data for further use (e.g., transmitting operational water data to a manufacturer of a water heater system 100 to create historical usage data).

In block 720, the water condition controller 500 can determine a normal operating range for each of the one or more water properties based on the baseline water data. For example, the water condition controller 500 can calculate a two-point calibration to obtain an operating curve. As another example, the water condition controller 500 can calculate partial derivates of each of the water properties with respect to time to determine when each of the one or more properties reaches steady-state. The determining and calculating can be performed by the water condition controller 500 using, for example, one or more processors. The water condition controller 500 can determine the normal operating range by calculating an average value for each of the water properties and determining a predetermined threshold away from the average value. For instance, the water condition controller 500 can determine an average flow rate value, and the predetermined threshold away from the average can be two standard deviations. The water condition controller 500 can determine the normal operating range by analyzing stored data in memory. The historical data can be logged or stored, for example, in the one or more storage devices, and retrieved by the water condition controller 500 when needed. Alternatively, the predetermined value can be a particular value (e.g., a user-inputted value). For example, a user can set the temperature of the system to never exceed 100° F. Therefore, the water condition controller 500 can determine an average temperature value, and the predetermined threshold is not to exceed 100° F. Alternatively, the normal operating range can be any value having a predetermined level of similarity to an average operating value for each of the one or more water properties (e.g., within a predetermined range of the average operating value).

In block 730, the water condition monitor 136 can begin measuring operational water data and relaying the measured data to the command module 520 via the transceiver 524. The operational water data can be indicative of a value of the one or more water properties during operation of the water heater system 100.

In block 740, the water condition controller 500 can compare the operational water data to the normal operating range at, for example, the one or more processors in the water condition controller 500. The water condition controller 500 can detect an anomaly indicative of a value of the one or more water properties being outside of the normal operating range. For example, if the normal operating range for temperature is not to exceed 100° F., and the temperature sensor on the water condition monitor 136 reads 112° F., the water condition controller 500 can designate that a temperature anomaly has been received. Alternatively, if there is no predetermined threshold value in the normal operating range, water condition controller 500 can determine an anomaly exists based on a value being outside of a predetermined level of similarity to the normal operating range.

In block 750, the water condition controller 500 can output one or more corrective actions in response to detecting the anomaly. The controller 530 can output the corrective actions to the water heater system 100 or any component thereof. The one or more corrective actions can comprise actions to correct the anomaly. For example, if the normal operating range for temperature is not to exceed 100° F., and the temperature sensor on the water condition monitor 136 reads 112° F., the water condition controller 500 instruct one or more water boilers to shut down. The one or more corrective actions can include, as non-limiting examples, emergency shut down of the water heater system 100, altering a flow rate, altering a temperature, and the like.

Upon detecting the anomaly, the water condition controller 500 can further transmit (e.g., via the transceiver) an alert to the user interface 510. The alert can be, for example, a blinking light, a warning on the screen, or an audible siren. The alert can comprise the anomaly value, the one or more corrective actions, and the normal operating range for the water property for which the anomaly was detected. The water condition controller 500 can automatically implement the one or more corrective actions, but the water condition controller 500 can also wait for user input before implementing the corrective actions. The user can indicate that the detected anomaly is normal and instruct the system to take no action. Alternatively, the user can instruct an emergency shutdown of the system if desired. The water condition controller 500 can receive the instructions from the user interface 510 or a user device and subsequently implement the desired corrective actions via output of instructions to the appropriate component(s). The method 700 can terminate after block 750. However, the method 700 can alternatively continue on to other method steps not shown. For example, the method 700 can then return to block 730 upon terminating block 750. In such a manner, continuous monitoring and correction of water properties in a water heater system 100 can be achieved.

As used in this application, the terms "module," "server," "processor," "memory," and the like are intended to include one or more computer-related units, such as but not limited to hardware, firmware, a combination of hardware and software, software, or software in execution. For example, a module may be, but is not limited to being, a process running on a processor, an object, an executable, a thread of execution, a program, and/or a computer. By way of illustration, both an application running on a computing device and the computing device can be a module. One or more modules can reside within a process and/or thread of execution and a module may be localized on one computer and/or distributed between two or more computers. In addition, these modules can execute from various computer readable media having various data structures stored thereon. The modules may communicate by way of local and/or remote processes such as in accordance with a signal having one or more data packets, such as data from one component interacting with another module in a local system, distributed system, and/or across a network such as the Internet with other systems by way of the signal.

Certain embodiments and implementations of the disclosed technology are described above with reference to block and flow diagrams of systems and methods according to example embodiments or implementations of the disclosed technology. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, may be repeated, or may not necessarily need to be performed at all, according to some embodiments or implementations of the disclosed technology. That is, the disclosed technology includes the performance of some or all steps of the methods and processes described herein in conjunction with the performance of additional steps not expressly discussed herein. Further, the present disclosure contemplates methods and processes in which some, but not all, steps described herein are performed.

While the present disclosure has been described in connection with a plurality of exemplary aspects, as illustrated in the various figures and discussed above, it is understood that other similar aspects can be used, or modifications and additions can be made to the described aspects for performing the same function of the present disclosure without deviating therefrom. For example, in various aspects of the disclosure, methods and compositions were described according to aspects of the presently disclosed subject matter. However, other equivalent methods or composition to these described aspects are also contemplated by the teachings herein. Therefore, the present disclosure should not be limited to any single aspect, but rather construed in breadth and scope in accordance with the appended claims.

Exemplary Use Cases

The following exemplary use cases describe examples of a typical user flow pattern. They are intended solely for explanatory purposes and not limitation.

A water condition monitor 136 can be placed in conjunction with a heater 130 for a user's pool 110. The water condition monitor 136 can be in communication with the pool ignition module 134, the heater 130, one or more pumps 120, and a water condition controller 500. The user can power on the pool heater system to begin heating and circulating the water in the pool. The water condition monitor 136 can begin monitoring properties of the water, such as temperature, flow rate, pH, and chlorine concentration. The water condition monitor 136 can continuously transmit the measured data to the water condition controller 500 via a transceiver 524. The water condition controller 500 can then perform a calibration to determine the normal operating range for temperature, flow rate, pH, and chlorine concentration. As data continues to be received from the water condition monitor 136, the water condition controller 500 can compare the received data to the normal operating range. Due to heavy rain fall entering the user's pool 110, for example, the additional water added to the system can reduce the chlorine concentration to unsafe and unsanitary levels. Upon detecting that the chlorine concentration has fallen outside of the normal operating range, the water condition controller 500 can designate an anomaly for the chlorine concentration property. Subsequently, the water condition controller 500 can output an emergency system shutdown as a corrective action. The water condition controller 500 can also transmit an alert to the user interface 510 on the user's mobile device that the chlorine concentration of the pool 110 is below the normal operating range and needs correction. The water condition controller 500 can also transmit the alert to the user interface 510 on a touchscreen on the heater 130 or elsewhere on the pool system 100. The alert can also comprise the value of the chlorine concentration compared to the normal operating range. The user can then add more chlorine to the system to remedy the anomaly.

A water condition monitor 136 can be placed in conjunction with a residential water heater system in a user's house. The water condition monitor 136 can be in communication with the water heater, one or more pumps, one or more valves, and a command module. The water in the residential water heater system can be circulating and heating as needed. The water condition monitor 136 can begin monitoring properties of the water, such as temperature, flow rate, pH, TDS, and lead concentration. The water condition monitor 136 can continuously transmit the measured data to the water condition controller 500 via a transceiver 524. The water condition controller 500 can then perform a calibration to determine the normal operating range for temperature, flow rate, pH, TDS, and lead concentration. As data continues to be received from the water condition monitor 136, the water condition controller 500 can compare the received data to the normal operating range. Due to frigid temperatures surrounding the house in the winter, for example, the cold temperatures of the pipes can cause the water to circulate at lower temperatures than desired. Upon detecting that the temperature has fallen outside of the normal operating range, the water condition controller 500 can designate an anomaly for the temperature property. Subsequently, the water condition controller 500 can output instructions to one or more boilers to ignite and begin heating the water in the water heater system as a corrective action. The water condition controller 500 can also transmit an alert to the user interface 510. The alert can cause a "currently heating" indicator light on the heater's touchscreen/keypad to blink. The alert can also be transmitted to a user's mobile device to indicate that the temperature is low and that corrective actions are being taken.

A water condition monitor 136 can be placed in conjunction with a heater 130 for a user's pool 110. The water condition monitor 136 can be in communication with the pool ignition module 134, the heater 130, one or more pumps 120, and a water condition controller 500. The user can power on the pool heater system to begin heating and circulating the water in the pool. The water condition monitor 136 can begin monitoring properties of the water, such as temperature, flow rate, pH, and chlorine concentration. The water condition monitor 136 can continuously transmit the measured data to the water condition controller 500 via a transceiver 524. The water condition controller 500 can then perform a calibration to determine the normal operating range for temperature, flow rate, pH, and chlorine concentration. A user can input in the user interface 510, a minimum flow rate of 50 gallons per hour for the pool circulation system. Therefore, the normal operating range for flow rate can be approximately 50 gal/hr±approximately 10 gal/hr (i.e., data indicative of normal operation can be in the range from approximately 40 gal/hr to approximately 60 gal/hr). As data continues to be received from the water condition monitor 136, the water condition controller 500 can compare the received data to the normal operating range. During use, users of the pool 110 may splash water out of the pool 110 reducing the volume of water in the system. The reduced water volume can cause air to enter the system, causing a rise in flow rate. Upon detecting that the flow rate has risen outside of the normal operating range, the water condition controller 500 can designate an anomaly for the flow rate property. Subsequently, the water condition controller 500 can output instructions to the pumps 120 to enter emergency shutdown. The water condition controller 500 can also cause an audible alert (e.g., via a speaker), such as a buzzing alarm, to engage, and can also transmit a notification to the user interface 510. For example, the water condition controller 500 can transmit a push notification to the user interface 510 on a user's mobile device indicating that the water flow rate has risen above the normal operating range and that the system has entered emergency shutdown. The user can then instruct the system, via the user interface 510, to perform corrective actions.

What is claimed is:

1. A water condition monitor apparatus comprising a fluid chemistry manifold, the fluid chemistry manifold comprising: an inlet; a first flow path having a first diameter and a second flow path different from the first flow path and having a second diameter greater than the first diameter, each of the first flow path and the second flow path being in fluid communication with the inlet; one or more probe apertures in fluid communication with the first flow path, the one or more probe apertures configured to detachably attach to at least a portion of a corresponding fluid chemistry probe, wherein a difference between the first diameter and the second diameter is configured to cause a constant fluid flow across a probe extending from at least one of the one or more probe apertures; an outlet in fluid communication with the first flow path and the second flow path; a first adjustable valve on an inlet side of the first flow path and configured to (i) selectively allow a fluid to flow therethrough when the fluid chemistry manifold is in an open state and (ii) direct the fluid to flow through the second flow path when the fluid chemistry manifold is in a closed state; and a second adjustable valve on an outlet side of the first flow path and configured to selectively (i) allow the fluid to flow therethrough when in the fluid chemistry manifold is in the open state and (ii) prevent the fluid from flowing therethrough when the fluid chemistry manifold is in the closed state, wherein the water condition monitor apparatus provides modular connection to a water heater system such that a user can detachably attach the water condition monitor apparatus to the water heater system.

2. The water condition monitor apparatus of claim 1, wherein the second flow path is an upper flow path and the first flow path is a lower flow path positioned at a lower height than the upper flow path.

3. The water condition monitor apparatus of claim 1 wherein the fluid chemistry manifold is configured to connect to and fluidly communicate with a water heater header.

4. The water condition monitor apparatus of claim 1, wherein the inlet and the outlet are configured to attach to a pool circulation system.

5. The water condition monitor apparatus of claim 1 further comprising a probe configured to detachably attach to the one or more probe apertures and fluidly communicate with the first flow path, wherein the probe comprises one or more of: a pH sensor, an oxidation reduction potential (ORP) sensor, and a total dissolved solids (TDS) sensor.

6. A water heater header cover comprising: an inlet; a flow path in fluid communication with the inlet and having a first diameter; two or more probe apertures located (i) on a face of the water heater header cover and (ii) along the flow path, each of the two or more probe apertures configured to detachably attach to at least a portion of a corresponding fluid chemistry probe such that a portion of each corresponding fluid chemistry probe can extend into the flow path; an outlet in fluid communication with the flow path; a bypass route from the inlet to the outlet having a second diameter and configured to transport fluid between the inlet and the outlet without entering the flow path, wherein a difference between the first diameter and the second diameter is configured to cause a constant fluid flow across a probe extending from at least one of the two or more probe apertures; a first adjustable valve disposed along the flow path at the inlet and configured to (i) selectively allow a fluid to flow into the flow path when in an open state and (ii) direct the fluid to flow through the-bypass route when in a closed state; and a second adjustable valve disposed along the flow path at the outlet and configured to selectively (i) allow the fluid to flow out of the flow path when in an open state and (ii) prevent the fluid from flowing through the flow path when in a closed state, wherein the inlet and the outlet are confiaured to detachably attach to piping used to circulate water throuah a water heater system.

7. The water heater header cover of claim 6 further comprising a probe configured to detachably attach to the two or more probe apertures and fluidly communicate with the flow path, wherein the probe comprises one or more of: a pH sensor, an oxidation reduction potential (ORP) sensor, and a total dissolved solids (TDS) sensor.

8. The water heater header cover of claim 6, wherein the first adjustable valve and the second adjustable valve are configured to selectively permit a predetermined amount of fluid flow through the flow path when water heater header cover is in the open state.

9. The water heater header cover of claim 6, wherein the flow path is further configured to be in fluid communication with a water heater header.

10. The water condition monitor apparatus of claim 1, wherein the first flow path has a first height and the second flow path has a second height such that the first flow path is positioned at a lower height than the second flow path.

11. The water condition monitor apparatus of claim 1, wherein the first adjustable valve and the second adjustable valve are configured to selectively permit a predetermined amount of fluid flow through the first flow path when the fluid chemistry manifold is in the open state.

12. The water condition monitor apparatus of claim 1, wherein the one or more probe apertures are disposed on the first flow path between the first adjustable valve and the second adjustable valve.

13. The water heater header cover of claim 6, wherein the two or more probe apertures are disposed on the flow path between the first adjustable valve and the second adjustable valve.

* * * * *